(12) United States Patent  (10) Patent No.: US 7,764,070 B2
Park et al.  (45) Date of Patent: Jul. 27, 2010

(54) BIO MOLECULAR DETECTION APPARATUS AND METHOD THEREOF

(75) Inventors: Tae-sik Park, Suwon-si (KR); Jung-ho Kang, Suwon-si (KR); Jong-hwa Won, Suwon-si (KR); Young-il Kim, Suwon-si (KR); Moon-chul Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 11/114,070

(22) Filed: Apr. 26, 2005

(65) Prior Publication Data

US 2005/0239120 A1  Oct. 27, 2005

(30) Foreign Application Priority Data

Apr. 27, 2004 (KR) .................. 10-2004-0029234

(51) Int. Cl.
  G01R 27/26 (2006.01)
  C12Q 1/68 (2006.01)
  C12M 1/34 (2006.01)
  G01N 27/26 (2006.01)
  G01N 27/00 (2006.01)
  C02F 1/40 (2006.01)

(52) U.S. Cl. .................. 324/668; 435/6; 435/287.2; 204/400; 204/403.01; 204/600; 422/82.02

(58) Field of Classification Search .......... 324/668; 435/6, 287.2; 204/400
  See application file for complete search history.

(56) References Cited

U.S. PATENT DOCUMENTS 4,728,882 A * 3/1988 Stanbro et al. .............. 324/687
5,632,957 A * 5/1997 Heller et al. ................ 422/68.1
6,856,125 B2 * 2/2005 Kermani .................... 324/71.1

(Continued)

FOREIGN PATENT DOCUMENTS

JP  05-188013 A  7/1993

(Continued)

OTHER PUBLICATIONS

Laurent G et al: "DNA Electrical Detection Based on Inductor Resonance Frequency in Standard CMOS Technology", European Solid-State Device Research, 2003 33rd Conference on. ESSDERC '03 Sep. 16-18, 2003, pp. 171-174, XP010676722.

(Continued)

*Primary Examiner*—Jeff Natalini
(74) *Attorney, Agent, or Firm*—Sughrue Mion, PLLC

(57) ABSTRACT

An apparatus and method of detecting bio molecular by measuring a variation of an electrical characteristic of a circuit having an inductance device and a capacitance device. The bio molecular detection method comprises providing a signal converting unit having at least one inductance device and at least one capacitance device connected with each other, disposing a biochip, which has capturing probe biomolecules attached to a substrate, at a location in the signal converting unit, and measuring an electrical characteristic of the signal converting unit, performing a coupling reaction of the biochip and a sample to be analyzed; and measuring an electrical characteristic of the signal converting unit after the coupling reaction.

16 Claims, 7 Drawing Sheets

U.S. PATENT DOCUMENTS

2002/0196009 A1    12/2002    Sewald

FOREIGN PATENT DOCUMENTS

| JP | 3447055 B2 | 7/2003 |
| JP | 2006-509208 A | 3/2006 |
| WO | WO 01/42508 A2 | 6/2001 |
| WO | WO 01/44828 A1 | 6/2001 |
| WO | WO 2004/010103 A2 | 1/2004 |
| WO | WO 2004/053491 A1 | 6/2004 |

OTHER PUBLICATIONS

K. Larsson et al., Magnetic Transducers in Biosensors and Bioassays, Analusis, 1999, vol. 27, No. 7, http://analusis.edpsciences.org or http://dx.doi.org/10.1051/analusis:1999270617.

* cited by examiner

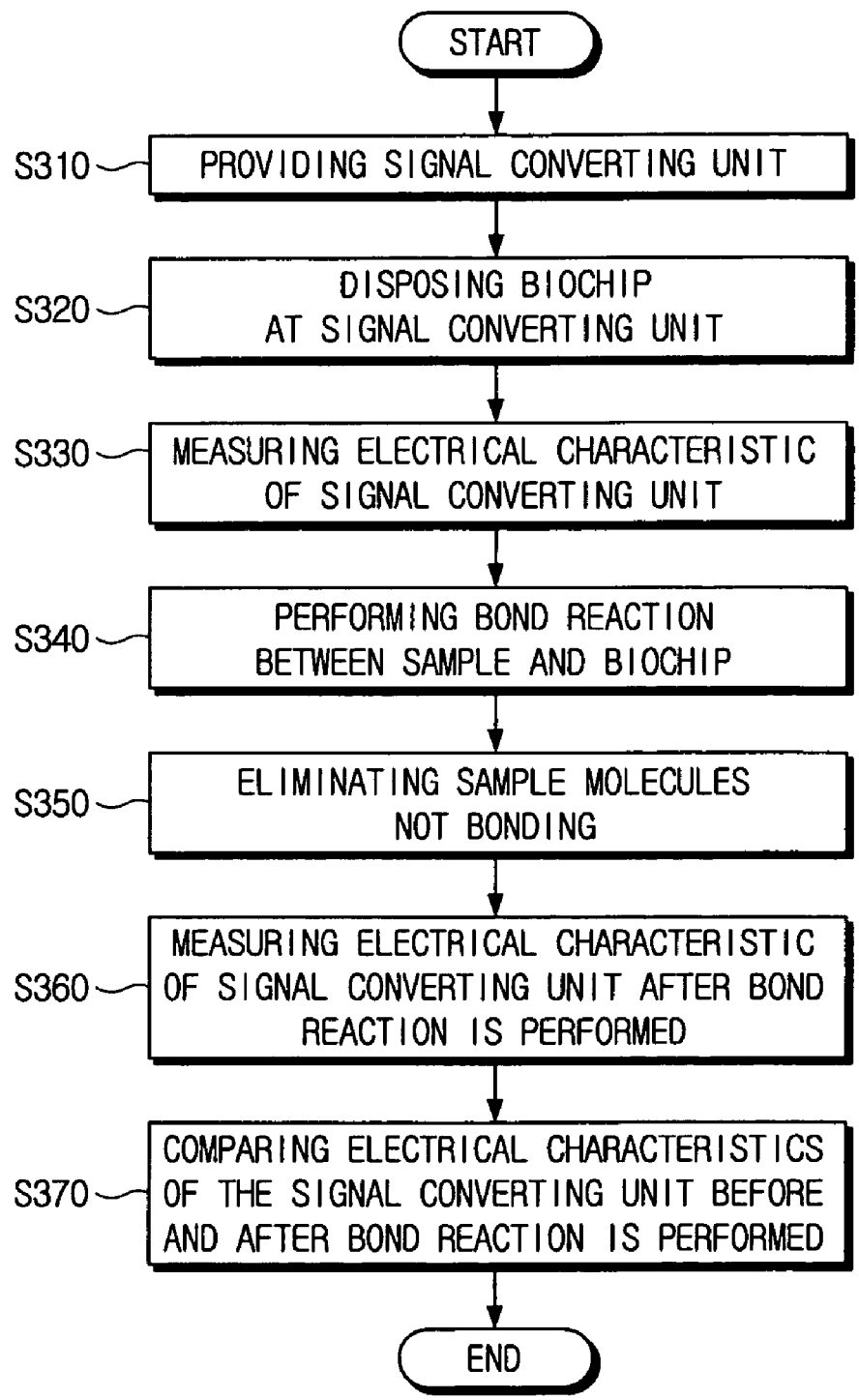

①: BEFORE BOND
②: AFTER BOND

BIO MOLECULAR DETECTION APPARATUS AND METHOD THEREOF

CROSS-REFERENCE TO RELATED APPLICATIONS

This application claims benefit under 35 U.S.C. §119 from Korean Patent Application No. 2004-29234, filed on Apr. 27, 2004, the entire content of which is incorporated herein by reference.

BACKGROUND OF THE INVENTION

1. Field of the Invention

The present invention relates to a bio molecular detection apparatus and a method thereof, and more particularly, to an apparatus and a method of measuring electrical characteristics of an inductance device and a capacitance device before and after the hybridization of a capturing probe and a sample to detect whether or not a biochip is coupled with the sample.

2. Description of the Related Art

A biochip refers to a biological microchip for analyzing a gene expression way, a distribution pattern and a mutation by arranging and attaching biomolecules, such as DNA, DNA fragment and RNA having the known sequences, on a small solid substrate formed of glass, silicon or nylon.

The biochip immobilizes materials, which function as capturing probes to search for specific gene information contained in a sample, on its surface. If the biochip reacts with the sample to be analyzed, the capturing probes of the biochip are respectively hybridized with materials of the sample. By detecting and interpreting whether or not the sample is coupled with the probes, information on the materials of the sample can be concurrently obtained.

Examples of technology relating to the biochip are a probe attaching and immobilization technology, a signal detecting technology, information processing technology and the like.

Examples of signal detecting method currently used are a laser-induced fluorescence detecting method, an electrochemical detecting method, a mass detecting method, a mechanical detecting method and the like. In the laser-induced fluorescence detecting method which is most widely used, a fluorescent material is coupled with a sample. After the coupling reaction of the capturing probe and the sample, a result of the coupling reaction is detected using a fluorescence detecting apparatus to optically determine whether or not the capturing probe is coupled with the sample. However, before the coupling reaction of the capturing probe and the sample, the laser-induced fluorescence detecting method requires a preprocessing reaction for coupling the fluorescent material with the sample. Therefore, the laser-induced fluorescence detecting method has a drawback in that sample loss or contamination can be caused. Further, the laser-induced fluorescence detecting method has a drawback in that it needs a complex optical detecting system for detecting whether or not the capturing probe is coupled with the sample after the coupling reaction of the capturing probe and the sample, and a high-priced measurement equipment. Further, the laser-induced fluorescence detecting method has a drawback in that it is difficult to accomplish miniaturization, and a digitalized output cannot be viewed.

In the electrochemical detecting method, it is detected whether or not a capturing probe is coupled with a sample by using an electrochemical reaction, that is, a reduction and oxidation reaction of other chemical materials on an electrode. The coupling reaction of the capturing probe and the sample is performed at the electrode. This method has a drawback in that it has a less detection capability than the fluorescence detecting method.

In the mass detecting method, an inter reaction between a capturing probe and a sample is electrically signalized and detected. As a typical example, there is an electrochemical Quartz Crystal Microbalance (QCM) detecting method for measuring a frequency variation depending on a mass of the capturing probe immobilized on quartz, which vibrates at a high frequency.

In the mechanical detecting method, a minutely assembled cantilever is used to measure a coupling strength between molecules before and after a capturing probe is coupled with a sample. However, this method has a drawback in that additional equipment such as a laser equipment is required to very minutely measure a refraction of a cantilever beam.

SUMMARY OF THE INVENTION

Accordingly, it is an aspect of the present invention to provide a bio molecular detection apparatus and method in which a preprocessing reaction prior to a bio molecular reaction is not separately required and a high-priced equipment is not separately required, and a detection result is provided in an electric signal to improve a detection capability for the coupling reaction.

The above aspect of the present invention is substantially realized by providing a bio molecular detection apparatus, apparatus comprising a signal converting unit having at least one inductance device and at least one capacitance device connected with each other, a biochip disposed at a predetermined area of the signal converting unit, an input port connected with one end of the signal converting unit, for receiving a signal for measuring an electrical characteristic of the signal converting unit, an output port connected with the other end of the signal converting unit, for outputting a signal from the signal converting unit, and a characteristic detecting unit connected with the output port, for measuring the electrical characteristic of the signal converting unit.

In accordance with another aspect of the present invention, there is provided a bio molecular detection method, the method comprising the steps of providing a signal converting unit having at least one inductance device and at least one capacitance device connected with each other, disposing a biochip, which has capturing probe biomolecules attached to a substrate, at a predetermined area of the signal converting unit, and measuring an electrical characteristic of the signal converting unit, performing a coupling reaction of the biochip and a sample to be analyzed, and measuring an electrical characteristic of the signal converting unit after the coupling reaction.

The method may further comprise steps of, after the coupling of the biochip and the sample, eliminating sample biomolecules not coupled with the biochip and excessive ones of sample biomolecules coupled with the biochip, and determining that the coupling of the biochip and the sample is performed when the electrical characteristic is different before and after the coupling reaction of the biochip and the sample.

Here, the signal converting unit may be operated as a passive or an active RF (Radio Frequency) device and an electrical device. For example, the signal converting unit may be operated any one of a frequency resonator, a phase modulator and a filter. And the characteristic detecting unit may be operated as a RF characteristic detector and an electrical characteristic detector. For example, the characteristic detecting unit may be operated any one of a resonant frequency detector, a phase detector, a loss characteristic detector, and a frequency characteristic detector.

The electrical characteristic may be any one of a resonant frequency, a phase, a signal magnitude, a loss characteristic, a RF characteristic, and a frequency characteristic of the signal converting unit.

The electrical characteristic may be any one of a resonant frequency, a phase, a signal magnitude, a loss characteristic, and a frequency characteristic of the signal converting unit, and the biochip may be disposed at one or more locations of between windings of the inductance device, between electrodes of the capacitance device, a top of the inductance device, and a top of the capacitance device.

Here, the signal converting unit is operated as the frequency resonator, the signal converting unit has a resonant frequency decreased and a signal magnitude increased at the resonant frequency after the coupling of the biochip and the sample.

BRIEF DESCRIPTION OF THE DRAWINGS

The above aspects and features of the present invention will be more apparent by describing certain embodiments of the present invention with reference to the accompanying drawings, in which:

FIG. 3 is a flowchart illustrating a bio molecular detection method according to an embodiment of the present invention;

DETAILED DESCRIPTION OF THE PREFERRED EMBODIMENTS

Figure 1A:
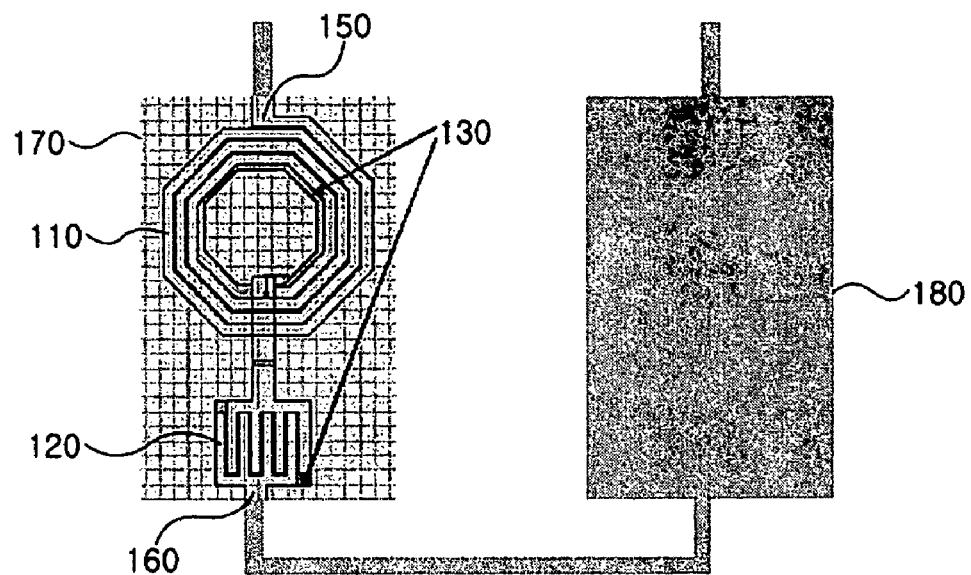
FIGS. 1A and 1B are sectional views illustrating a bio molecular detection apparatus according to an embodiment of the present invention.

Hereinafter, an embodiment of the present invention will be described in detail with reference to the accompanying drawing figures.

In the following description, same drawing reference numerals are used for the same elements even in different drawings. The matters defined in the description such as a detailed construction and elements are merely provided to assist in a comprehensive understanding of the invention. Thus, it is apparent that the present invention can be carried out without those defined matters. Also, well-known functions or constructions are not described in detail since they would obscure the invention in unnecessary detail.

Figure 1B:
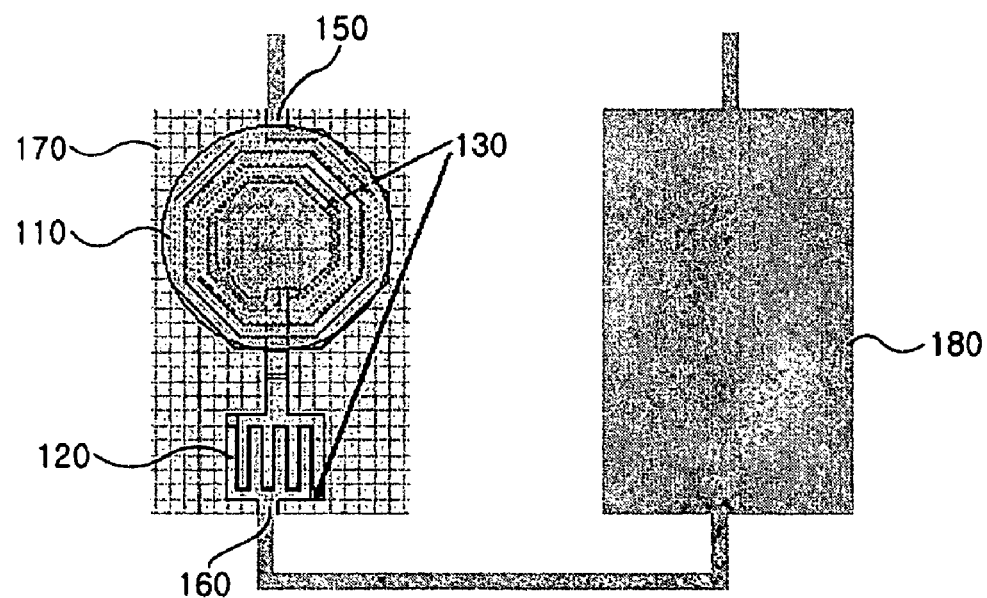

FIGS. 1A and 1B are sectional views illustrating a bio molecular detection apparatus according to an embodiment of the present invention.

As shown in FIGS. 1A and 1B, a signal converting unit 170 comprises the inductance device 110 and the capacitance device 120 connected in series. The signal converting unit 170 varies its electrical characteristic depending on whether or not coupling is performed, to detect the bio molecular. Here, the electrical characteristic of the signal converting unit 170 refers to a resonant frequency, a phase, a signal magnitude, a frequency characteristic, a loss characteristic, a RF (Radio Frequency) characteristic and the like. The signal converting unit 170 comprises at least one inductance device 110 and at least one capacitance device 120 series or parallel-connected with each other. The signal converting unit 170 can be implemented as a frequency resonator, a phase modulator and a filter. FIGS. 1A and 1B illustrate the frequency resonator having at least one inductance device 110 and at least one capacitance device 120 connected in series.

Additionally, the signal converting unit 170 comprises a biochip 130 to which capturing probe biomolecules are immobilized. The biochip 130 is disposed at one or more locations between windings of the inductance device 110, between electrodes of the capacitance device 120, a top of the inductance device 110, and a top of the capacitance device 120. In FIG. 1A, the biochips 130 are disposed between the windings of the inductance device 110 and between the electrodes of the capacitance device 120. In FIG. 1B, the biochips 130 are disposed at the top of the inductance device 110 and between the electrodes of the capacitance device 120.

Meanwhile, an input port 150 is connected with the inductance device 110 to receive a signal for measuring the electrical characteristic of the signal converting unit 170. An output port 160 is connected with the capacitance device 120 and is also connected with a characteristic detecting unit 180. The output port 160 outputs the signal inputted through the input port 150. A characteristic of a frequency outputted through the output port 160 is different depending on whether or not the biochip 130 is coupled with the sample.

The characteristic detecting unit 180 connected with the output port 160 detects the electrical characteristic outputted from the output port 160. In case where the signal converting unit 170 is implemented as the frequency resonator, the phase modulator and the filter, the characteristic detecting unit 180 is respectively implemented as a resonant frequency detector, a phase detector, and a frequency characteristic detector.

Figure 2A:
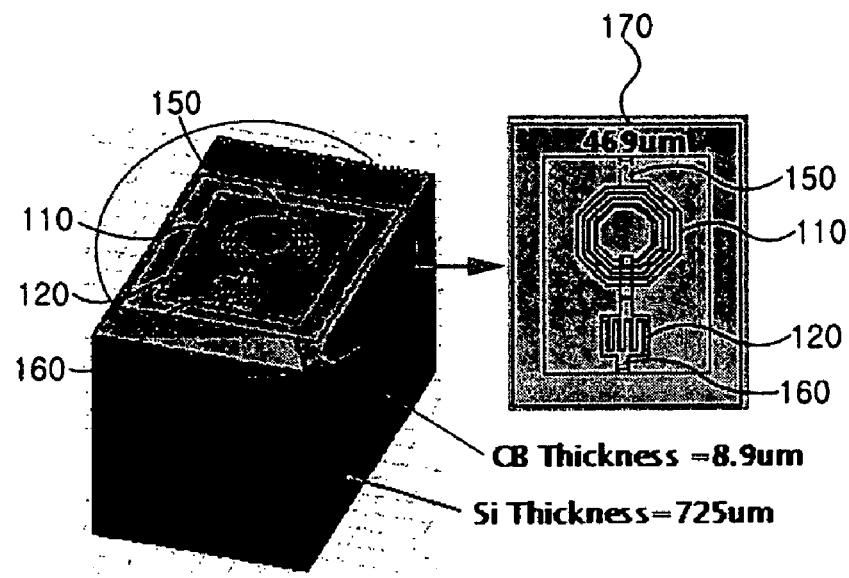
FIGS. 2A and 2B are views illustrating a signal converting unit of a bio molecular detection apparatus according to an embodiment of the present invention.
Figure 2B:
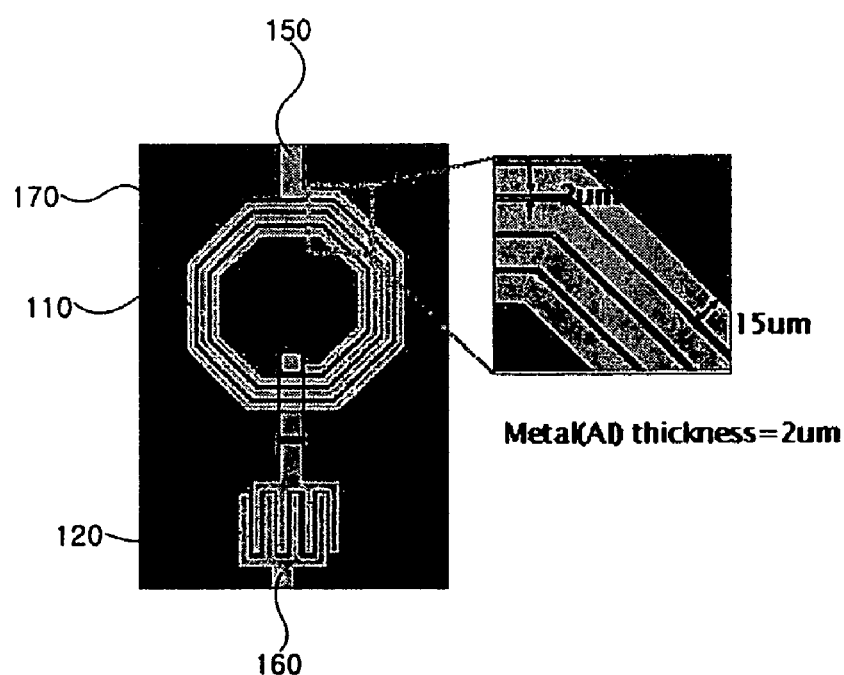

FIGS. 2A and 2B are views illustrating the signal converting units of the bio molecular detection apparatus according to a preferred embodiment of the present invention.

In FIGS. 2A and 2B, the signal converting unit 170 comprises the inductance device 110 and the capacitance device 120 connected in series, to function as the frequency resonator. FIG. 2A illustrates the signal converting unit 170 formed on BenzoCycloButene (BCB) formed on silicon (Si). The BCB has a thickness of 8.9 μm and a dielectric constant ($\in_r$) of 2.65. Silicon (Si) has a thickness of 725 μm and a dielectric constant ($\in_r$) of 11.9. The input port 150 has an impedance of 50 ohm, and the signal converting unit 170 has a width of 469 μm.

In FIG. 2B, the inductance device 110 of the signal converting unit 170 shown in FIG. 2A has a winding interval of 2 μm, a winding width of 15 μm, and a winding thickness of 2 μm.

FIG. 3 is a flowchart illustrating a bio molecular detection method according to an embodiment of the present invention.

Firstly, the biochip 130 is provided by immobilizing materials, which function as capturing probes to search for specific information of the sample, to a surface of a substrate (S310). After that, the inductance device 110 and the capacitance device 120 are connected to form the signal converting unit 170. Here, the inductance device 110 and the capacitance device 120 can be connected in series or parallel, or a plurality of the inductance devices 110 and the capacitance devices 120 can be used to implement the signal converting unit 170 as the resonator, the phase modulator and the filter.

Next, the biochip 130 is disposed at one or more locations of between the windings of the inductance device 110, between the electrodes of the capacitance device 120, the top of the inductance device 110, and the top of the capacitance device 120 (S320).

After that, the electrical characteristic of the signal converting unit 170 having the biochip 130 is measured. That is, the electrical characteristic of the signal converting unit 170, such as the resonant frequency, the signal magnitude at the resonant frequency, the phase, and the frequency characteristic, a loss characteristic, a RF characteristic, is measured before the coupling is performed, that is, before the biochip 130 is reacted with the sample to be analyzed (S330). This is to compare with the electrical characteristic of the signal converting unit 170 after the coupling, to detect an amount of the coupling and whether or not the coupling is performed.

Next, the sample 140 to be analyzed is reacted with the biochip 130. Here, the sample 140 refers to DNA, RNA, protein, biomocules and the like.

In case where the biomolecules of the sample 140 have corresponding forms to the biomolecules of the biochip 130, the coupling is performed between the sample 140 and the biochip 130. Excessive ones of the biomolecules reacting with the biomolecules of the biochip 130 and the biomolecules of the sample 140 not reacting with the biomolecules of the biochip 130 are eliminated (S350).

Additionally, after the biomolecules of the biochip 130 are coupled with the biomolecules of the sample 140, the electrical characteristic of the signal converting unit 170, such as the resonant frequency, the signal magnitude, the phase, a loss characteristic, and a RF characteristic is measured (S360).

If a coupling reaction is performed between the biochip 130 and the sample 140, the electrical characteristic of the signal converting unit 170 is varied. Therefore, specific values of the electrical characteristic of the signal converting unit 170 are compared with each other before and after the bond reaction to detect the amount of the coupling and whether or not the coupling is performed (S370). In case where the signal converting unit 170 is implemented as the frequency resonator, the coupling reaction can be detected using the resonant frequency and the signal magnitude at the resonant frequency, which are varied before and after the coupling reaction. In case where the signal converting unit 170 is implemented as the phase modulator, the coupling reaction can be detected using the phase, which is varied before and after the coupling reaction. Further, in case where the signal converting unit 170 is implemented as the filter, the coupling reaction can be detected using the frequency characteristic, which is varied before and after the coupling reaction. As described above, in case where the signal converting unit 170 is implemented as the frequency resonator, the coupling reaction can be detected using the resonant frequency increased or the signal magnitude at the resonant frequency decreased after the coupling reaction.

Figure 4A:
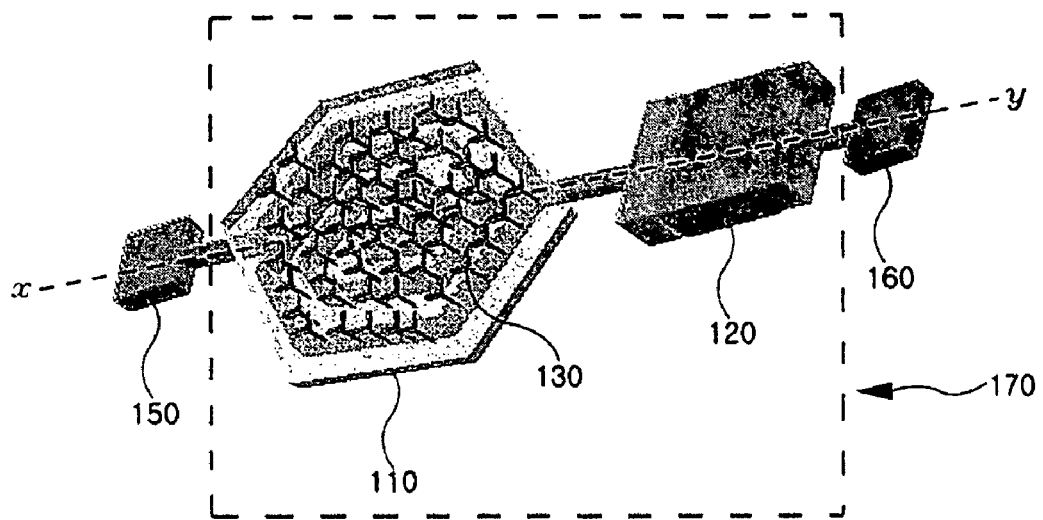
FIGS. 4A to 4F are views illustrating a bio molecular detection method according to an embodiment of the present invention.
Figure 4B:
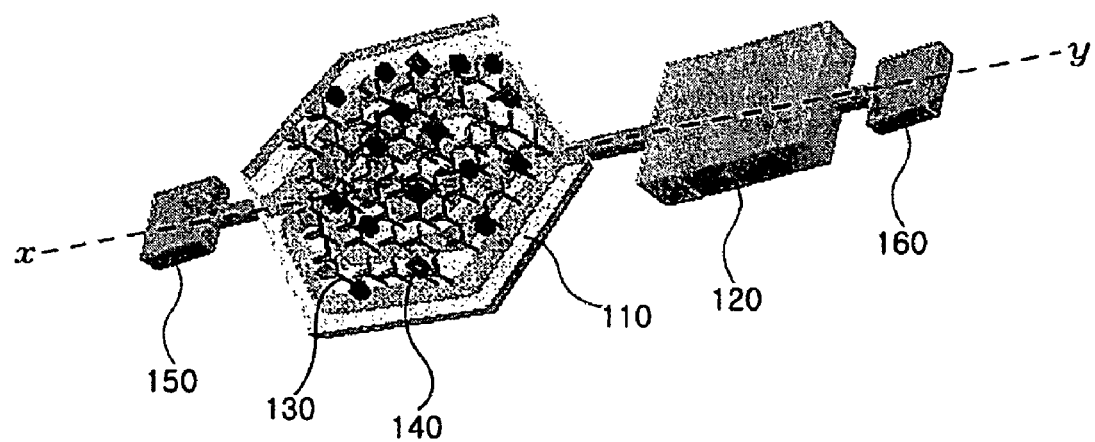
Figure 4C:
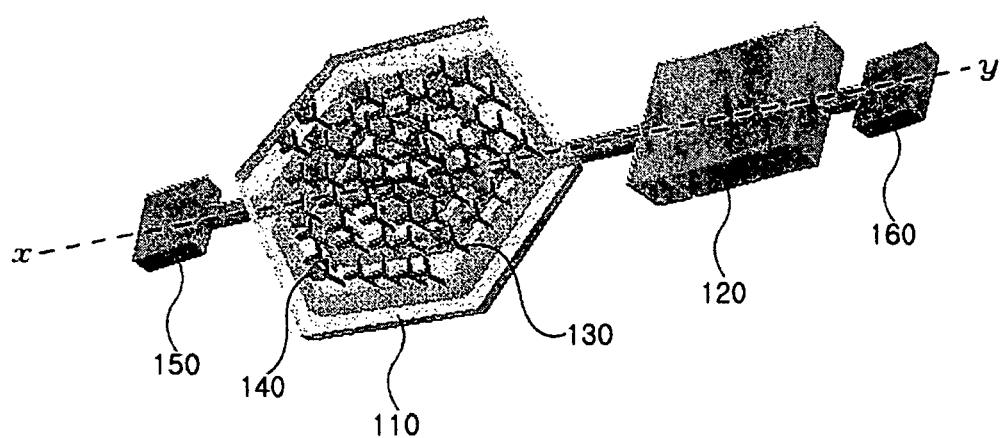
Figure 4D:
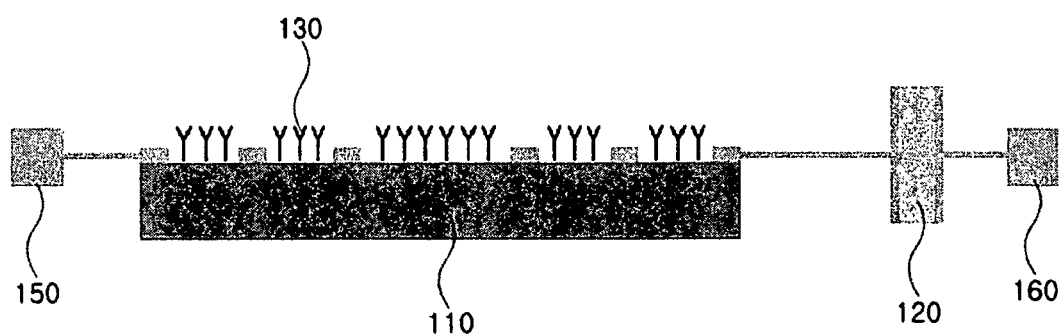
Figure 4E:
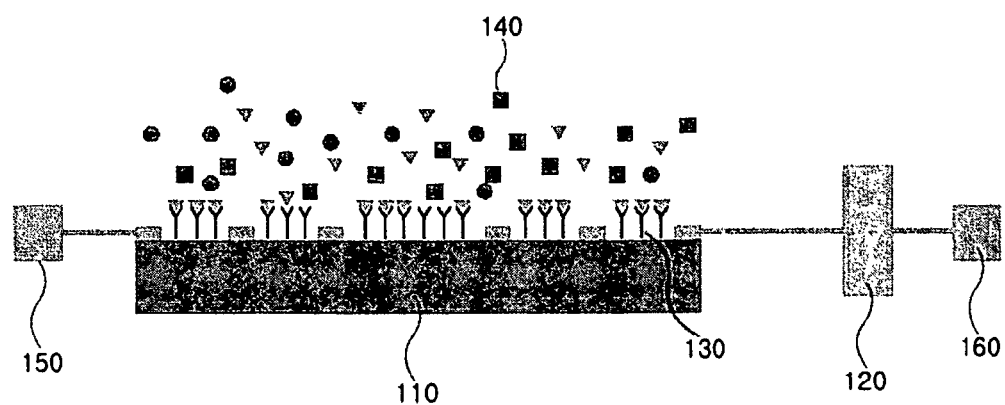
Figure 4F:
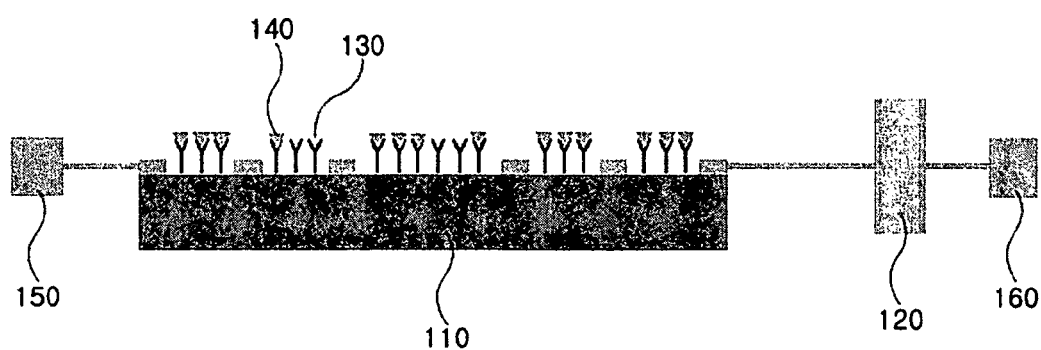

FIGS. 4A to 4F are views illustrating the bio molecular detection method according to an embodiment of the present invention. FIGS. 4A and 4C are perspective views illustrating the bio molecular detection method, and FIGS. 4D to 4F are sectional views taken along X-Y axes of FIGS. 4A to 4C.

As shown in FIGS. 4A and 4D, the inductance device 110 and the capacitance device 120 are series-connected to form the signal converting unit 170. The biochip 130 is provided between the windings of the inductance device 110. After that, a high-frequency signal is inputted to the input port 150 to measure the electrical characteristic of the signal converting unit 170 before the coupling.

FIGS. 4B and 4E illustrate the signal converting units 170 when the coupling reactions are performed. In case where the sample 140 has the molecules can couple with the molecules immobilized to the biochip 130, the sample 140 is coupled with the biochip 130.

FIGS. 4C and 4F illustrate the signal converting units 170 after the coupling reactions are performed, that is, after the sample biomolecules not coupled with the biochip 130 and the excessive ones of the sample biomolecules coupled with the biochip 130 are eliminated. After the coupling is performed, the signal is inputted to the input port 150 to measure the electrical characteristic of the signal converting unit 170. Whether or not the coupling reaction is performed is detected, by comparing with each other output values of the output port 160 before and after the coupling reaction is performed.

Figure 5A:
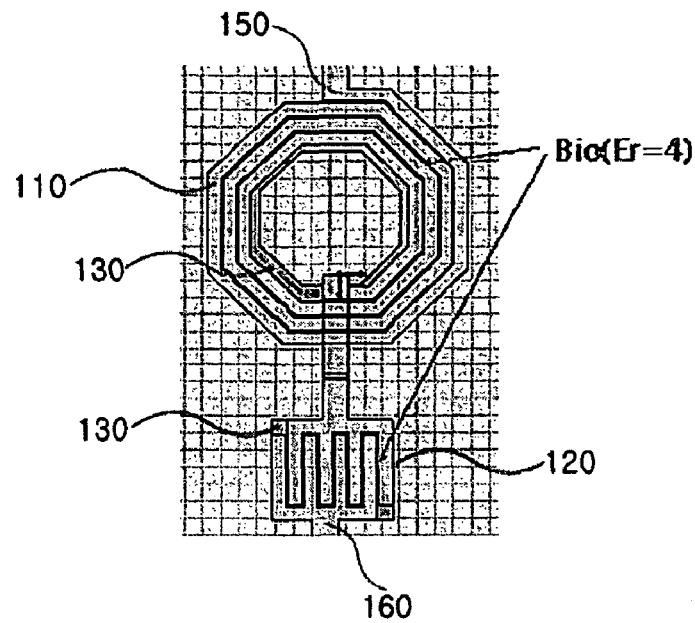
FIG. 5A is a sectional view illustrating a signal converting unit having a dielectric constant, which is varied before and after coupling is performed.

FIG. 5A is a sectional view illustrating the signal converting unit having the dielectric constant, which is varied before and after the coupling is performed.

In FIG. 5A, the biochips 130 are provided between the windings of the inductance device 110 and between the electrodes of the capacitance device 120. In case where the dielectric constant of air is provided as the dielectric constant between the windings of the inductance device 110, a varied dielectric constant of 4 is obtained after the coupling reaction. A difference between the dielectric constants before and after the coupling reaction is converted into an electrical signal.

Figure 5B:
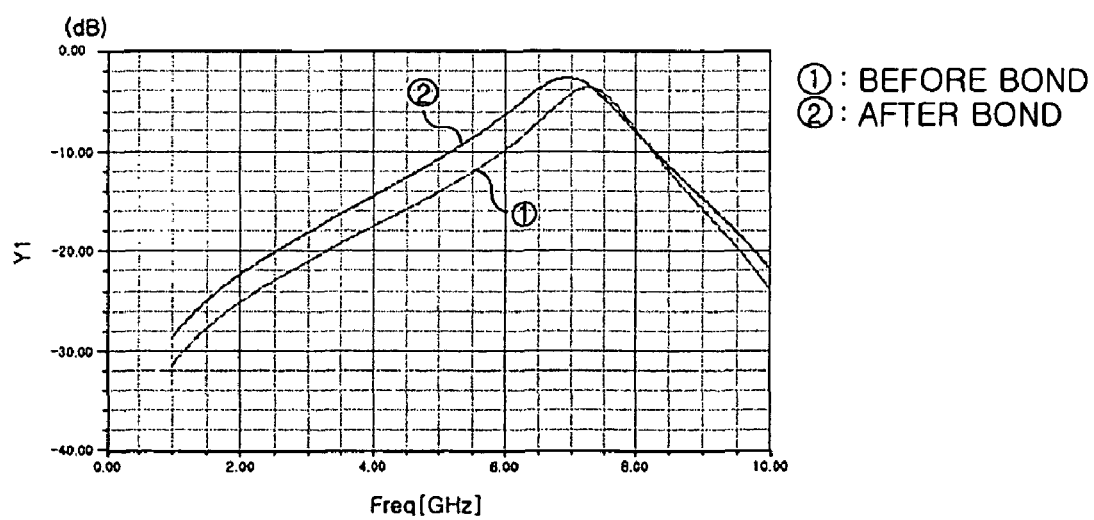
FIG. 5B is a graph illustrating a frequency characteristic of a signal converting unit before and after coupling is performed.

FIG. 5B is a graph illustrating the frequency characteristic of the signal converting unit before and after the coupling is performed.

In case where the signal converting unit 170 is implemented as the frequency resonator, the resonant frequency is decreased from 7.27 GHz before the coupling (①) to 6.95 GHz after the coupling (②). Further, the signal magnitude is increased from −3.16 dB before the coupling (①) to −2.61 dB after the coupling (②). That is, in case where the resonant frequency is decreased or the signal magnitude is increased after the coupling reaction, it can be appreciated that the coupling reaction is performed.

As described above, the present invention can measure the electrical characteristic of a device having the inductance device and the capacitance device to obtain a detected result of the coupling in the electrical signal, thereby improving the detection capability for the coupling reaction.

Further, the present invention does not separately require the pretreatment reaction as in a conventional fluorescence detecting method, and a high-priced equipment as in a conventional mechanical detecting method and the conventional fluorescence detecting method. Accordingly, the bio molecular detection time can be reduced.

The foregoing embodiment and advantages are merely exemplary and are not to be construed as limiting the present invention. The present teaching can be readily applied to other types of apparatuses. Also, the description of the embodiments of the present invention is intended to be illustrative, and not to limit the scope of the claims, and many alternatives, modifications, and variations will be apparent to those skilled in the art.

What is claimed is:

1. A bio molecular detection apparatus, the apparatus comprising:
   a signal converting unit having at least one inductance device and at least one capacitance device connected with each other;
   a biochip disposed in the signal converting unit;
   an input port connected with one end of the signal converting unit, for receiving a signal for measuring an electrical characteristic of the signal converting unit;

an output port connected with an other end of the signal converting unit, for outputting a signal from the signal converting unit; and a characteristic detecting unit connected with the output port, for measuring the electrical characteristic of the signal converting unit, the at least one inductance device covers a surface of a substrate, and comprises a spiral shaped microstrip formed on a surface of a layer having a lower dielectric constant than the substrate, the at least one capacitance device comprises two tandem electrodes formed apart from the inductance device on the surface of the layer having a lower dielectric constant at a predetermined distance so as to be opposite and interlocked to each other, and the at least one inductance device and the at least capacitance device are connected in series to each other.

2. The biomolecular detection apparatus of claim 1, wherein the signal converting unit is one of a RF (Radio Frequency) device and an electrical device.

3. The biomolecular detection apparatus of claim 1, wherein the signal converting unit is one of a frequency resonator, a phase modulator, and a filter.

4. The biomolecular detection apparatus of claim 1, wherein the biochip is disposed in at least in one location selected from: between windings of the inductance device and a top of the inductance device.

5. The biomolecular detection apparatus of claim 1, wherein the biochip is disposed in at least in one location selected from: between electrodes of the capacitance device and a top of the capacitance device.

6. The biomolecular detection apparatus of claim 1, wherein the electrical characteristic is one of a resonant frequency, a phase, a signal magnitude, a frequency characteristic, a loss characteristic, and a RF (Radio Frequency) characteristic of the signal converting unit.

7. The biomolecular detection apparatus of claim 1, wherein the characteristic detecting unit is one of a RF detector and an electrical device.

8. The biomolecular detection apparatus of claim 1, wherein the characteristic detecting unit is one of a resonant frequency detector, a phase detector, a frequency characteristic detector, and a loss characteristic detector.

9. A bio molecular detection method comprising:
providing a signal converting unit having at least one inductance device and at least one capacitance device connected with each other;
disposing a biochip in the signal converting unit, the biochip having captured probe biomolecules attached to a substrate;
measuring an electrical characteristic of the signal converting unit;
performing a coupling reaction of the biochip and a sample to be analyzed; and
measuring an electrical characteristic of the signal converting unit after the coupling reaction,
the at least one inductance device covers a surface of a substrate, and comprises a spiral shaped microstrip formed on a surface of a layer having a lower dielectric constant than the substrate,
the at least one capacitance device comprises two tandem electrodes formed apart from the inductance device on the surface of the layer having a lower dielectric constant at a predetermined distance so as to be opposite and interlocked to each other, and
the at least one inductance device and the at least capacitance device are connected in series to each other.

10. The method according to claim 9, wherein sample biomolecules not coupled with the biochip and excess sample biomolecules coupled with the biochip are eliminated before measuring the electrical characteristic.

11. The method according to claim 9, further comprising:
in case where the electrical characteristic is different before and after the coupling reaction, determining that there is coupling of the biochip and the sample.

12. The method according to claim 9, wherein the electrical characteristic is one of a resonant frequency, a phase, a signal magnitude, a loss characteristic, and a frequency characteristic of the signal converting unit.

13. The method according to claim 9, wherein the signal converting unit is one of a frequency resonator, a phase modulator, and a filter.

14. The method according to claim 13, wherein in case where the signal converting unit is a frequency resonator, the signal converting unit has a resonant frequency decreased and a signal magnitude increased at the resonant frequency after the biochip and the sample form a bio-bond.

15. The method according to claim 9, wherein the biochip is at least one location selected from: between windings of the inductance device, between electrodes of the capacitance device, a top of the inductance device, and a top of the capacitance device.

16. The method according to claim 9, wherein the characteristic detecting unit is one of a resonant frequency detector, a phase detector, a loss characteristic detector, and a frequency characteristic detector.

* * * * *